(12) United States Patent
Daerr et al.

(10) Patent No.: US 10,983,071 B2
(45) Date of Patent: Apr. 20, 2021

(54) PULSE-WIDTH MODULATION FOR A PHOTON SCANNING APPARATUS

(71) Applicant: KONINKLIJKE PHILIPS N.V., Eindhoven (NL)

(72) Inventors: Heiner Daerr, Hamburg (DE); Roland Proksa, Neu Wulmstorf (DE); Frank Bergner, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/305,446

(22) PCT Filed: May 2, 2018

(86) PCT No.: PCT/EP2018/061135
§ 371 (c)(1),
(2) Date: Nov. 29, 2018

(87) PCT Pub. No.: WO2018/202675
PCT Pub. Date: Nov. 8, 2018

(65) Prior Publication Data
US 2020/0319121 A1    Oct. 8, 2020

(30) Foreign Application Priority Data

May 4, 2017 (EP) .................... 17169416

(51) Int. Cl.
*G01N 23/04* (2018.01)
*A61B 6/03* (2006.01)
(Continued)

(52) U.S. Cl.
CPC .......... *G01N 23/046* (2013.01); *A61B 6/032* (2013.01); *G01T 7/005* (2013.01); *A61B 6/582* (2013.01)

(58) Field of Classification Search
CPC ...... A61B 6/032; A61B 6/582; G01N 23/046; G01T 7/005
See application file for complete search history.

(56) References Cited

U.S. PATENT DOCUMENTS 6,178,226 B1   1/2001   Hell
8,964,940 B2   2/2015   Caruso
(Continued)

FOREIGN PATENT DOCUMENTS

CN   105246240 A   1/2016
JP   2005094108 A   4/2005
(Continued)

OTHER PUBLICATIONS

Robert Alvarez, "Estimator for photon counting energy selective x-ray imaging with multibin pulse height analysis" by Med Phys. May 2011; 38(5): 2324-2334.
(Continued)

*Primary Examiner* — Mark R Gaworecki
(74) *Attorney, Agent, or Firm* — Larry Liberchuk

(57) ABSTRACT

The present invention relates to a photon scanning apparatus comprising a photon source (2) to emit a photon beam (4), a photon detector (6) to detect photons emitted from the photon source (2). The photon source (2) is adapted to emit the photon beam (4) in accordance with a predetermined pulse width modulation scheme at a predetermined flux rate, wherein the pulse width modulation scheme defines pulse widths of the photon beam (4) for respective positions of the photon source (2) and the photon detector around a central axis (R) and an object to be scanned. The photon detector (6) is adapted to start detecting photons with a delay relative to the photon source starting to emit photons and to finish detecting photons prior to the photon source stopping to emit
(Continued)

photons. The photon scanning apparatus thus only has to be calibrated for the predetermined flux rate.

8 Claims, 3 Drawing Sheets

(51) Int. Cl.
*G01T 7/00* (2006.01)
*G01N 23/046* (2018.01)
*A61B 6/00* (2006.01)

(56) References Cited

U.S. PATENT DOCUMENTS

| 9,877,694 | B2 | 1/2018 | Honda |
| 2005/0089135 | A1 | 4/2005 | Toth |
| 2011/0026668 | A1 | 2/2011 | Wu |
| 2012/0121063 | A1 | 5/2012 | Proksa |
| 2014/0367861 | A1 | 12/2014 | Uchino |
| 2015/0038839 | A1 | 2/2015 | Schaefer |
| 2015/0063529 | A1 | 3/2015 | Taguchi |
| 2016/0089102 | A1 | 3/2016 | Wang |
| 2016/0113603 | A1 | 4/2016 | Schirra |
| 2016/0324494 | A1 | 11/2016 | Roessl |
| 2017/0045632 | A1 | 2/2017 | Thran |

FOREIGN PATENT DOCUMENTS

| JP | 2016143592 A | 8/2016 |
| WO | 2010/058330 | 5/2010 |

OTHER PUBLICATIONS

Plewes, et al., "Grid controlled x-ray tube switching time: implications for rapid exposure control", Med Phys. Sep.-Oct. 1984;11(5):693-6.

PULSE-WIDTH MODULATION FOR A PHOTON SCANNING APPARATUS

CROSS REFERENCE TO RELATED APPLICATIONS

This application is the U.S. National Phase application under 35 U.S.C. § 371 of International Application No. PCT/EP2018/061135, filed May 2, 2018, published as WO 2018/202675 on Nov. 8, 2018, which claims the benefit of European Patent Application Number 17169416.9 filed May 4, 2017. These applications are hereby incorporated by reference herein.

FIELD OF THE INVENTION

The present invention generally relates to photon scanning apparatuses and methods for operating the same and more particularly to calibrating photon-counting imaging detectors described with particular application to spectral computed tomography (CT).

BACKGROUND OF THE INVENTION

A conventional CT scanner includes an X-ray tube mounted on a rotatable gantry opposite a detector array located across an examination region. The rotatable gantry, and hence the X-ray tube, rotates around the examination region. The X-ray tube is configured to emit X-ray radiation. A radiation intensity profile shaper such as the well-known "bow-tie" filter attenuates the emitted X-ray radiation directed towards the examination region to a greater degree at peripheral regions, relative to a more central region, thereby reducing the flux at the outer regions, which improves radiation efficiency.

A source collimator collimates the filtered X-ray radiation, producing a radiation beam in the direction of the examination region. The filtered radiation beam traverses the examination region (and an object of interest therein), and is detected by a detector array, which includes a one or two dimensional array of detector pixels. The detector pixels, in response, generate and output signals indicative of the detected radiation. The signal can be reconstructed to generate volumetric image data. Additionally, the volumetric image data can be processed to generate one or more images of the object of interest.

A spectral CT scanner has included the above-discussed elements with the addition of photon-counting detector pixels (sensor material e.g., CdTe, CdZnTe, etc.) (and, optionally multiple sources, kVp switching, etc.). Unfortunately, the bow-tie filter alters the primary beam spectrum of the X-ray source. That is, while the spectrum in front of the bow-tie filter can be considered homogenous for all angles, spectral distortions are caused by the bow-tie filter material, and the shape of the bow-tie filter results in variations in fan angle direction.

One common approach of calibrating photon counting detectors is to map a known set of absorber compositions to detector signals, which are subsequently used, e.g. in form of a look-up table, for material decomposition. This technique thus requires a calibration phantom whose complexity increases with number of absorber materials, since each material combination that may occur in measured objects has to be realized in the calibration procedure or an equivalent pair of absorbers as described in "Estimator for photon counting energy selective x-ray imaging with multibin pulse height analysis" by Alvarez, Robert E., Med. Phys. 38 (5), pages 2324-2334, May 2011.

For example, in order to acquire calibration data for medical CT, a calibration procedure has to be performed, where all combinations of all relevant thicknesses of bone, e.g., 0-10 cm, and all relevant thicknesses of soft tissue, e.g., 0-40 cm, have to be taken into account. A suitable procedure would be to produce two step phantoms of materials with similar X-ray attenuation properties as bone and soft tissue, e.g., aluminum and a polymer, respectively, and acquire data for all combinations of step numbers of both step phantoms.

In order to allow varying properties of individual pixels or the angle dependence of the X-ray spectrum, the calibration data has to be acquired for all detector pixels. For example, a step phantom comprising 10 material thicknesses each, a total of 100 individual measurements would have to be made for each pixel. With a third material, e.g., iodine or another contrast agent, a third material would have to be included, adding an additional dimension to the calibration procedure.

Another approach comprises a detector model to estimate the photon counts for each material combination. Here, the detector model needs to be calibrated using a calibration phantom with one or more materials. Regardless of the chosen approach, each detector pixel needs to be calibrated due to pixel-to-pixel variation within the detector and changes of the primary spectrum due to the bow-tie already mentioned above. Using photon counting detectors, the described calibration is necessary not only for different material combinations, but also for different combinations of X-ray tube currents and X-ray tube acceleration voltages due to the effect of pulse pile-up. Advanced CT scanners use dynamic dose modulation to adapt the X-ray flux for each projection according to the attenuation profile of a patient. One prominent example is the patient's shoulder with a strong attenuation of horizontal rays and a lower attenuation of vertical rays. The modulation aims for homogeneous noise distribution yielding improved dose utility. Dose modulation is an indispensable feature in medical imaging as it adopts the X-ray flux to the patient's anatomy. Dose modulation may be achieved by modulating the X-ray tube current. Accordingly, the working point of the detector would vary from view to view, which would require a proper calibration for all occurring working point settings of the scanner during the scan, since the detected counts are a non-linear function of the incoming photon flux.

A new technique called X-ray tube grid switching (GS) allows for ultra-fast binary (on/off) X-ray flux modulation of the X-ray tube output. With switching times below 1 μsec, the flux modulation can be used to do sparse angular sampling for CT. In addition, it enables a kind of pulse width modulation to radiate the detector only for a limited time interval within an integration period, thus allowing to expose a patient to X-ray radiation as little as necessary.

For photon counting CT scanners pulse width modulation cannot be easily applied to modulate doses. For high flux imaging, photon counting detectors will suffer from the effect of pulse pile-up. Photon counts may get lost due to the dead time of the detector or two lower energetic photons may be counted as one photon. Wherein the response curve of an ideal photon counting detector would increase linearly with an increasing flux, a real photon counting detector's response curve is non-linear. The pile up effect during operation with a stable flux thus differs from the pile up effect during rise up of the photon flux at the beginning of a pulse as well as during ramp down of the flux at the end of a pulse.

In that respect, US patent application US 2016/0324494 A1 discloses an imaging system which includes a radiation source with a focal spot that emits a beam of X-ray photons that traverses an examination region. The imaging system further includes a photon counting detector array that detects a sub-set of the X-ray photons that traverse an examination region. The imaging system further includes a controller that generates and transmits a pause signal, in response to a calculated drop in an intensity of the emitted the beam of X-ray photons below a predetermined intensity level, which causes the photon counting detector array to pause detecting the sub-set of the X-ray photons. The imaging system further includes a counter that counts, for each of a plurality of counting periods, the X-ray photons of the sub-set detected by the photon counting detector array in the corresponding counting period.

Further, US patent application US 2005/0089135 A1 discloses a system and method of diagnostic imaging is provided that includes determining a position of a subject in a scanning bay and tailoring X-ray attenuation such that the specific position of the subject is taken into consideration. In accordance with the concept disclosed therein, a proper attenuation filter configuration is automatically selected, patient centering is corrected and noise prediction errors are corrected, thereby increasing dose efficiency and tube output.

SUMMARY OF THE INVENTION

It is thus an object of the present invention to provide a photon scanning apparatus and a method of operating the same with effective dose modulation that requires a reduced calibration effort.

The objective is achieved by an apparatus and a method according to the independent claims.

According to an aspect of the present invention, a photon scanning apparatus is presented. The apparatus comprises a photon source to emit a photon beam, a photon detector positioned in the propagation direction of the photon beam to detect photons emitted from the photon source, wherein the photon source and the photon detector are commonly rotatable around a central axis, wherein the photon source is adapted to emit the photon beam in accordance with a predetermined pulse width modulation scheme at a predetermined flux rate, wherein the pulse width modulation scheme defines pulse widths of the photon beam for respective positions of the photon source and the photon detector around and along the central axis and an object to be scanned, and wherein the photon detector is adapted to start detecting photons for a time period corresponding to the predetermined pulse width with a delay relative to the photon source starting to emit photons and to finish detecting photons prior to the photon source stopping to emit photons.

By applying pulse width modulation excluding the time periods in which the photon flux is ramped up and down at the beginning and end of each pulse from the photon counting process, the photon detector can be operated at a single flux rate. Thus, the detector only needs to be calibrated for the predetermined flux rate which significantly reduces the calibration effort required for conventional flux modulation.

The photon scanning apparatus may preferentially be a spectral CT scanner. The photon source and photon detector may be parts of a gantry which is adapted to rotate around a central axis. Furthermore, the gantry may also be movable in a direction along the central rotation axis to allow a helical movement along the central axis. Alternatively, the gantry may only be rotatable around the central axis, and support means positioned along the central axis can be moved with respect to the gantry along the rotational axis. Both arrangements allow scans of a patient positioned at the central axis in a helical manner. The photon source is adapted to emit a photon beam, preferentially a polychromatic photon beam, in accordance with a predetermined pulse width modulation scheme. Pulse width modulation schemes can be realized via so called grid-switching mechanisms as described in "Grid controlled x-ray tube switching time: Implications for rapid exposure control" by Plewes, D. B. and Vogelstein, E., Med. Phys. 11 (5), pages 693-696, September/October 1984. The pulse width modulation scheme is patient specifically determined for respective positions of the photon source and detector arrangement, e.g. positions of the gantry, and depends on the region of interest to be scanned, e.g. the anatomical region or organ to be examined. The photon scanning apparatus may comprise a memory storing a look-up table, wherein the look-up table associates photon beam pulse widths for respective regions of interest and patient conditions with respective positions of the photon source, e.g. the gantry. In a simple pre-scan, also referred to as CT scout scan or scanogram, the position of the region of interest is determined. The same region of interest, for example the same organ, may still require a different dosage depending on the patient conditions, e.g. body type (obesity, age, heath, etc.) and the resolution required for a diagnosis. The respective input may be provided by a user of the photon scanning apparatus. Based on the determined patient specific pulse width modulation scheme, the photon source is adapted to emit a photon pulse of the respective duration. The photon detector is adapted to start detecting photons with a delay relative to the photon source starting to emit photons. The delay is chosen such that the photon detector starts counting photons when the photon flux is stable. Pile up effects occurring for the stable flux rate are accounted for in the reconstruction, e.g. the photon counting detector is calibrated for this working point. The pile up effects occurring during rise up and ramp down of the flux are different and can therefore not be accounting for during reconstruction. During rise up and ramp down of the photon flux the pile up effect might cause the detector response to allegedly count more photons than actually incoming. Therefore, the respective time intervals needed for rise up and ramp down of the photon flux are excluded from the measurement periods. The delay time may be determined in advance either during manufacturing or during calibration. The photon detector is further adapted to finish detecting photons prior to the photon source stopping to emit photons. The photon detector may stop counting photons simultaneously with the photon source receiving a command to finish photon emission. Upon receipt of this command the photon flux will be ramped down. By stopping the photon counting at the same time as the photon flux is ramped down, it is ensured that no pile up effects influence the photon counts. Thus, the photon scanning apparatus can exploit pulse width modulation and thus only requires a single calibration or least only calibrations for a few working points which decreases the calibration effort significantly compared to conventional dose modulation schemes.

In an embodiment the photon source is adapted to issue a command indicative of an emission period corresponding to a predetermined pulse width to the photon detector upon starting to emit the photon beam, and the photon detector is adapted to start counting photons upon a predetermined delay after receipt of the command until the end of the emission period.

With the end of the emission period, the photon flux is not immediately set to zero but is ramping down. During this time pulse pile up effects occur such that the photon detector is adapted to stop counting photons with the end of the regular emission period and thus before the flux is decreased.

In an embodiment the photon source is adapted to issue a command indicative of an emission time corresponding to a predetermined pulse width to the photon detector with a predetermined delay after having started to emit photons, and the photon detector is adapted to start counting photons upon receipt of the command for a time period that is shorter than the predetermined pulse width by a predetermined amount. In this embodiment, the initial delay is controlled by the photon source. This may be in particular advantageous if the rise time differs and is sensed and estimated by the photon source based on the slope of the rise curve until the nominal flux rate is reached. The photon source may additionally correct the nominal pulse width for the determined delay and send this corrected pulse width to the photon detector, which then simply switches on after receipt of the command and off after the time period corresponding to the corrected pulse width has passed. By concentrating the delay and correction logic at one side, the logic on the other side may be simpler, in this case the logic at the photon detector side. However, the logic to correct the time period corresponding to the corrected pulse width may also be implemented at the photon detector side. In both cases, the photon detector stops photon counting before the photon flux is ramped down.

In an embodiment the photon scanning apparatus further comprises a control unit to determine a rotational position of the photon source and photon detector in accordance with the pulse width modulation scheme and to issue control commands to the photon source and the photon detector indicative of respective operation periods corresponding to a particular pulse width wherein the photon source is adapted to start emitting photons upon receipt of the control command for an emission period corresponding to the particular pulse width, and the photon detector is adapted to start counting photons upon a predetermined delay after receipt of the control command for a detection period that ends with the emission period. The control unit may issue simultaneously control commands to the photon source and to the photon detector indicative of respective operation periods corresponding to a particular pulse width. The logic to determine the delay and the shortened detection period that ends together with the emission period to avoid counting photons while the photon flux is ramped down, may again be comprised at the photon detector side to avoid the need of calculating the delay at both sides. Alternatively, the logic may also be distributed at the control unit and the photon detector such that the control unit already provides a command indicating a detection period that ends with the emission period.

In an embodiment the photon scanning apparatus further comprises a control unit to determine a rotational position of the photon source in accordance with the pulse width modulation scheme and to issue a first control command to the photon source, wherein the photon source is adapted to start emitting the photon beam upon receipt of the first control command for a predetermined first period of time, and to issue a second control command to the photon detector wherein the photon detector is adapted to start counting photons upon receipt of the second control command for a predetermined second period of time that ends with the first period of time. In this embodiment, the trigger logic at the photon source and the photon detector is kept as simple as possible. Upon receipt of respective commands the photon source and the photon detector start operation. With regard to the determination of the second period of time, the respective logic may again be provided at the control unit or at the photon detector side.

According to an aspect of the present invention a method for operating a photon scanning apparatus at a predetermined flux rate comprising a photon source to emit a photon beam according to a predetermined pulse width modulation scheme and a photon detector positioned in the propagation direction of the photon beam to detect photons emitted from the photon source, wherein the photon source and the photon detector are commonly rotatable around a central axis, are presented. The method comprises scanning the object using a pulse width according to the pulse width modulation, wherein the photon detector starts detecting photons for a time period corresponding to the predetermined pulse width with a predetermined delay relative to the photon source starting to emit photons, and wherein the photon detector finishes detecting photons prior to the photon source stopping to emit photons.

It shall be understood that the photon scanning apparatus of claim 1, the method for operating a photon scanning apparatus of claim 7 and the computer program of claim 8 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
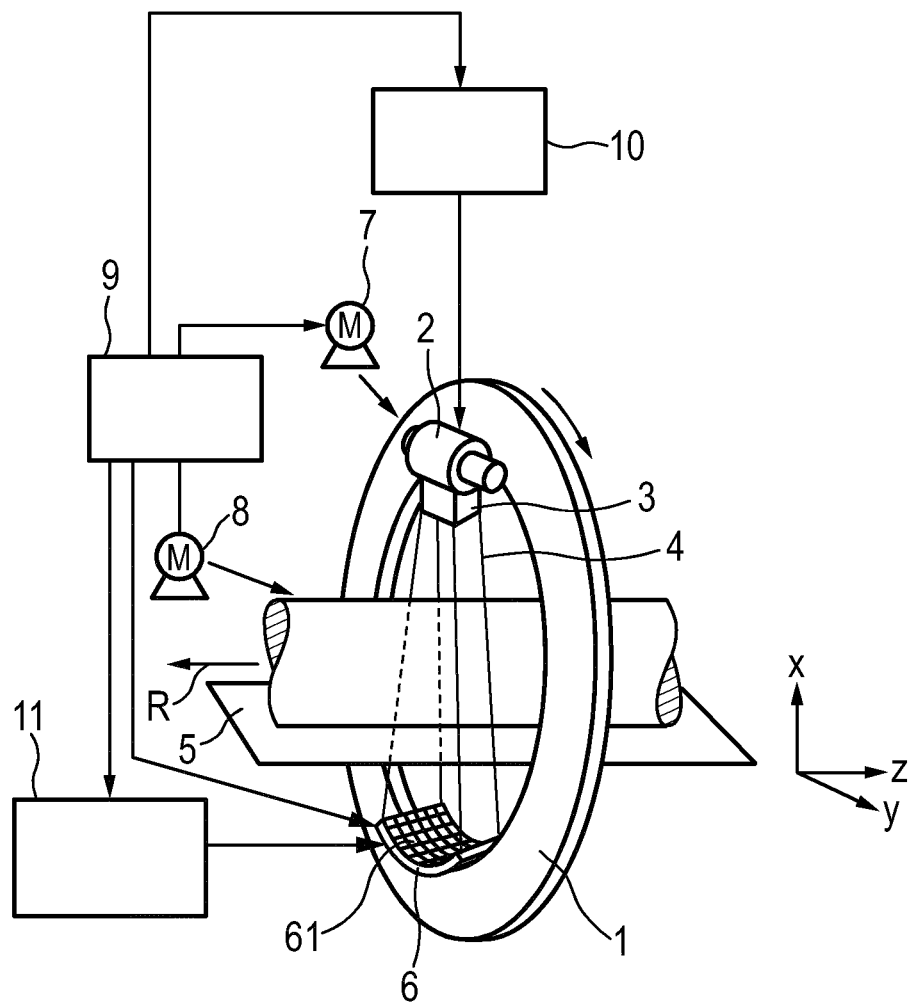
FIG. 1 schematically and exemplarily shows a photon scanning apparatus according to an embodiment of the present invention.

FIG. 1 shows an embodiment of a photon scanning apparatus according to the present invention, in particular a spectral CT imaging system for medical applications and examination of a patient. The CT imaging system shown in FIG. 1 includes a gantry 1 which is capable of rotation about an axis of rotation R which extends parallel to the z direction. The radiation source 2, in particular a conventional X-ray tube, for instance with rotating tungsten anode is mounted on the gantry 1. The X-ray tube 2 is provided with a collimator device 3 which forms a shaped radiation beam 4, such as a fan, cone wedge or any other predetermined shape, from the radiation produced by the X-ray tube 2. The radiation traverses an object (not shown), such as a patient positioned on a support 5, in a region of interest in a cylindrical examination zone (imaging region). After having traversed the examination zone, the X-ray beam 4 is incident on an X-ray detector unit 6, in this embodiment a two-dimensional photon-counting detector having a plurality of detector cells 61, which is mounted on the gantry 1 and which converts incident X-ray radiation into detection signals.

The gantry 1 is driven at a preferably constant but adjustable angular speed by a motor 7. A further motor 8 is provided for displacing the object, e.g. the patient who is arranged on a patient table in the examination zone 5, parallel to the direction of the axis of rotation R or the z axis as indicted in FIG. 1. These motors 7, 8 are controlled by a control device 9, for instance such that the radiation source 2 and the examination zone 5 move relative to one another along a helical trajectory. However, it is also possible that the object or the examination zone 5 is not moved, but that only the X-ray source 2 is rotated.

Figure 2:
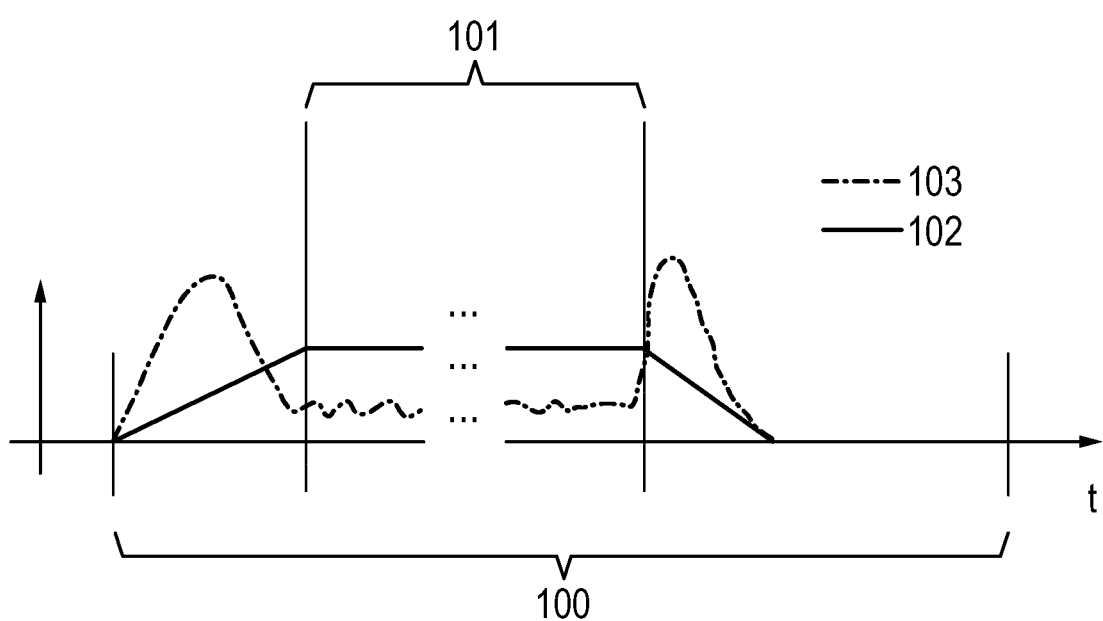
FIG. 2 schematically and exemplarily shows a nominal integration period of a photon detector and the photon flux and photon counts for a photon pulse.

For controlling the X-ray source 2, in particular for modulating the X-ray flux that is provided by said X-ray source 2, a source control device 10 is provided. This source control device 10 ensures that the X-ray flux emitted by the X-ray source 2 is provided at a pre-determined flux level for a predetermined duration or pulse width. The pulse width can be realized using a grid switching arrangement at the photon source. Such a grid switching arrangement is shown in FIG. 2 of WO 2010/058330 A1 which is incorporated herein by reference in its entirety. Wherein WO 2010/058330 A1 discloses to use the grid switching mechanism to block the electron beam in case of the detection of any damaging effect, the grid may also be used to modulate the pulse widths.

Since the photon detector 6 has to be separately calibrated for each working point, the X-ray source 2 and photon detector 6 are preferably calibrated for a predetermined number of working points, for instance five working points. Wherein in principle a single working point, e.g. one current per acceleration voltage, would be sufficient since the dose will be modulated by the exposure time, e.g. the pulse width, it may be appropriate to define more than one working point to avoid very large exposure times for objects with high absorption characteristics or very short integration time and high amount of pulse pile-up for low absorbing objects. For instance, in order to obtain spectral CT images from regions in the extremities only a low dose is needed, such that a short pulse width and/or a low flux rate are sufficient. The anatomical region of the stomach on the other hand requires a much higher dose in order to obtain an image with acceptable noise. Thus, if the same low flux rate would be used as for imaging of the legs or arms, the pulse width would be much higher. Longer exposure times prolong the procedure as a whole which is undesirable in itself. Furthermore, a patient may slightly move during exposure, e.g. when breathing in or out, which may lead to a decrease in the precision of the reconstructed image. Thus, it may be advantageous to have three to five working point of the X-ray flux for a given X-ray tube acceleration voltage for respective regions with significantly differing absorption characteristics.

Thus, depending on the region of interest an appropriate working point is determined and a patient is scanned in a so called scout scan to roughly determine where the organ or region of interest is located. For that region, a patient specific pulse width modulation scheme is determined, defining respective positions of the X-ray tube 2 and thus also of the photon counting detector 6 on the opposite side of the gantry 1 and corresponding exposure times or pulse widths for each position. The pulse widths may be determined from a look-up table defining pulse widths for respective gantry positions and imaging subjects, such as specific organs, etc., as well as patient specific parameters like age, size/volume, etc. and absorption characteristics determined during the scout scan.

Figure 3:
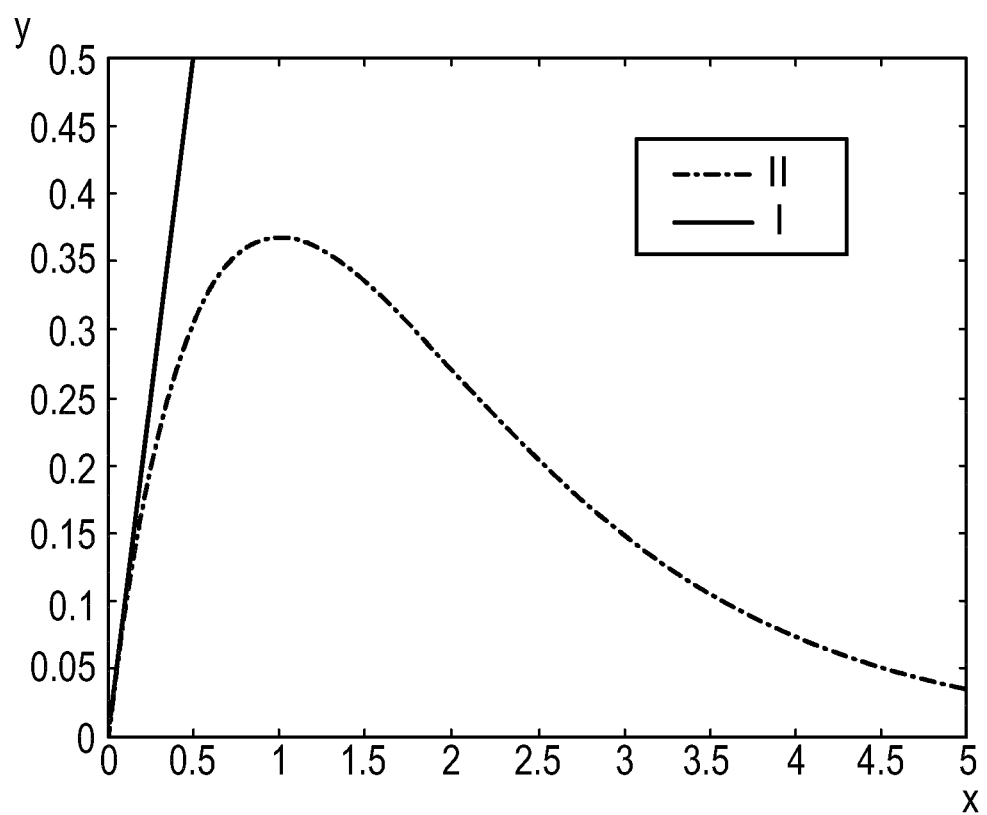
FIG. 3 schematically and exemplarily shows a typical response curve for a photon counting detector affected by pile-up compared to a response curve for an ideal photon counting detector without pulse pile-up.

When performing the actual scan, the control device 9 provides respective commands to the motors 7 and 8 to position the support 5 and rotate the gantry 1 around the examination zone. For predetermined positions, the control device 9 issues operation commands to the source control device 10 that initiate the corresponding emission of a radiation beam 4 by the X-ray source 2 for a time period corresponding to the predetermined pulse width. The control device 9 simultaneously issues respective commands to a detector control device 11 that initiates operation of the photon detector 6 with a predetermined delay, e.g. 1-3 μsec, compared to the initiation of the X-ray source 2. Furthermore, the detector control device 11 stops operation of the photon detector 6 after the time period corresponding to the predetermined pulse width has been reached, e.g. the detector 6 stops operation together with or even slightly before the X-ray source 2. The photons arriving at the detector during the time required for the X-ray source 2 upon receipt of a start or stop command until the current that controls the photon emission is ramped up or down, are thus not counted by the photon detector 6 as indicated in FIG. 2. The curve 102 shows the photon flux, the curve 103 shows the photons counted by the detector. In the example given in FIG. 2 the gantry 1 rotates with a speed that provides a certain nominal integration period 100, e.g. 400 μsec for each position. According to the pulse width modulation scheme previously determined the pulses emitted from the X-ray source 2 may be much shorter than the nominal integration period 100, e.g. 200 μsec. However, upon switching the X-ray source to an ON state, it takes a little while until there is a stable photon flux. The detector's photon counting rate firstly rises linearly but then falls off due to pile up. FIG. 3 shows exemplarily a typical pulse pile-up curve for an ideal photon counting detector I and for a real photon counting detector II. The x-axis shows the input rate, the y-axis the output rate. The axes are normalized to the dead time of the detector T. An ideal photon counting detector would have identical input and output rates. A real photon detector, however, starts with a linear response and encounters counting losses with increasing input rates. For very high rates, the detector saturates and the output rate decreases (behind the input rate times τ equals 1). For a stable flux, the counting losses due to pile up can be accounted for, e.g. the detector is calibrated for this working point and the calibration is taken into account during image reconstruction. However, the detector response during rise up and ramp down times would significantly impact the overall counting rate. These miscounts cannot be easily corrected for in the image reconstruction. Therefore, the actual integration period 101 of the photon detectors 6 starts with a delay relative to the start of the X-ray source ON period and stops before the photon flux is ramped down as shown in FIG. 2. If the rise times and the drop-down times are stable, respective hardware triggers may be programmed with the determined delay time such that whenever a start command and a corresponding pulse width is received from the device control unit 9, the detector control device 11 will trigger the detector's operation with the programmed delay and stop the detector's operation with the end of the nominal pulse width.

Alternatively, the logic to delay the trigger command may also be implemented in the control unit 9 instead of the detector control device 11. In that case, the detector control device 11 would trigger the operation of the photon detector 6 immediately upon receipt of the respective command from the control unit 9. However, the control unit 9 would issue the start command with a slight delay compared to the start command issued to the source control device 10.

In yet an alternative implementation, the source control device 10 and the detector control device 11 may communicate with one another wherein the source control device 10 issues a respective trigger command to the detector control device 11 when it starts operating the X-ray source 2 for a predetermined pulse width. The detector control device 11 starts operation of the photon detectors 6 with a predetermined delay upon receipt of the command and stops the photon detector 6 when the time corresponding to the nominal pulse width has been reached. Again, the delay logic could also be implemented in the source control device 10 which may alternatively issue the start command to the detector control device 11 with a predetermined delay.

The control of the photon scanning apparatus in accordance with the method for operating the photon scanning apparatus can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A photon scanning apparatus, comprising:
a photon source to emit a photon beam; and
a photon detector positioned in the propagation direction of the photon beam to detect photons emitted from the photon source, wherein the photon source and the photon detector are commonly rotatable around a central axis;
wherein the photon source is configured to emit the photon beam in accordance with a predetermined pulse width modulation scheme at a predetermined flux rate, wherein the pulse width modulation scheme defines pulse widths of the photon beam for respective positions of the photon source and the photon detector around and along the central axis and an object to be scanned, and
wherein the photon detector is configured to start detecting photons for a time period corresponding to the predetermined pulse width with a delay relative to the photon source starting to emit photons and to finish detecting photons prior to the photon source stopping to emit photons.

2. The photon scanning apparatus according to claim 1, wherein the photon source is configured to issue a command indicative of an emission period corresponding to a predetermined pulse width to the photon detector upon starting to emit the photon beam, and the photon detector is configured to start counting photons upon a predetermined delay after receipt of the command.

3. The photon scanning apparatus according to claim 1, wherein the photon source is configured to issue a command indicative of an emission time corresponding to a predetermined pulse width to the photon detector with a predetermined delay after having started to emit photons, and the photon detector is configured to start counting photons upon receipt of the command for a time period that is shorter than the predetermined pulse width by a predetermined amount.

4. The photon scanning apparatus according to claim 1, further comprising a control unit to determine a rotational position of the photon source in accordance with the pulse width modulation scheme and to issue a control command to the photon source and the photon detector indicative of respective operation periods corresponding to a particular pulse width, wherein the photon source is configured to start emitting photons upon receipt of the control command for an emission period corresponding to the particular pulse width, and the photon detector is configured to start counting photons upon a predetermined delay after receipt of the control command for a detection period that ends with the emission period.

5. The photon scanning apparatus according to claim 1, further comprising a control unit to determine a rotational position of the photon source in accordance with the pulse width modulation scheme and to issue a first control command to the photon source, wherein the photon source is configured to start emitting the photon beam upon receipt of the first control command for a predetermined first period of time, and to issue a second control command to the photon detector, wherein the photon detector is configured to start counting photons upon receipt of the second control command for a predetermined second period of time that ends a predetermined amount before the first period of time.

6. The photon scanning apparatus according to claim 1, wherein the photon scanning apparatus is a spectral computed tomography scanning apparatus.

7. A method for operating a photon scanning apparatus at a predetermined flux rate comprising a photon source to emit a photon beam according to a predetermined pulse width modulation scheme and a photon detector positioned in the propagation direction of the photon beam to detect photons emitted from the photon source, wherein the photon source and the photon detector are commonly rotatable around a central axis, the method comprising:
scanning the object using a pulse width according to the pulse width modulation, wherein the photon detector starts detecting photons for a time period corresponding to the predetermined pulse width with a predetermined delay relative to the photon source starting to emit photons, and wherein the photon detector finishes detecting photons prior to the photon source stopping to emit photons.

8. A non-transitory computer-readable medium having executable instructions stored thereon which, when executed by at least one processor, cause the at least one processor to perform a method for operating a photon scanning apparatus at a predetermined flux rate comprising a photon source to emit a photon beam according to a predetermined pulse width modulation scheme and a photon detector positioned in the propagation direction of the photon beam to detect photons emitted from the photon source, wherein the photon source and the photon detector are commonly rotatable around a central axis, the method comprising:

scanning the object using a pulse width according to the pulse width modulation, wherein the photon detector starts detecting photons for a time period corresponding to the predetermined pulse width with a predetermined delay relative to the photon source starting to emit photons, and wherein the photon detector finishes detecting photons prior to the photon source stopping to emit photons.

\* \* \* \* \*